(12) United States Patent
Shelley et al.

(10) Patent No.: US 7,223,977 B2
(45) Date of Patent: May 29, 2007

(54) METHOD OF MEASURING THICKNESS OF AN OPAQUE COATING USING NEAR-INFRARED ABSORBANCE

(75) Inventors: Paul H. Shelley, Lakewood, WA (US); Wes W. Quigley, Auburn, WA (US)

(73) Assignee: The Boeing Company, Chicago, IL (US)

( * ) Notice: Subject to any disclaimer, the term of this patent is extended or adjusted under 35 U.S.C. 154(b) by 92 days.

(21) Appl. No.: 11/130,627

(22) Filed: May 16, 2005

(65) Prior Publication Data

US 2005/0263704 A1 Dec. 1, 2005

Related U.S. Application Data

(63) Continuation-in-part of application No. 10/304,640, filed on Nov. 26, 2002, now Pat. No. 6,903,339.

(51) Int. Cl.
G01N 21/35 (2006.01)

(52) U.S. Cl. .................................. 250/339.01
(58) Field of Classification Search ........... 250/339.01, 250/339.11
See application file for complete search history.

(56) References Cited

U.S. PATENT DOCUMENTS

| 3,017,512 | A | 1/1962 | Wolbert |
| 3,631,526 | A | 12/1971 | Brunton et al. |
| 3,693,025 | A | 9/1972 | Brunton |
| 3,973,122 | A | 8/1976 | Goldberg |
| 3,994,586 | A | 11/1976 | Sharkins et al. |
| 4,015,127 | A | 3/1977 | Sharkins |
| 4,527,062 | A | 7/1985 | Novinson |
| 4,549,079 | A | 10/1985 | Terasaka et al. |
| 4,625,114 | A | 11/1986 | Bosacchi et al. |
| 4,791,296 | A | 12/1988 | Carpio |
| 4,800,279 | A | 1/1989 | Hieftje et al. |
| 5,015,856 | A | 5/1991 | Gold |
| 5,091,647 | A | 2/1992 | Carduner et al. |
| 5,142,151 | A | 8/1992 | Varnell et al. |
| 5,208,648 | A | 5/1993 | Batchelder et al. |
| 5,289,266 | A | 2/1994 | Shih et al. |
| 5,358,333 | A | 10/1994 | Schmidt et al. |
| 5,381,228 | A | 1/1995 | Brace |
| 5,714,758 | A * | 2/1998 | Neu ...................... 250/339.08 |
| 5,795,394 | A | 8/1998 | Belotserkovsky et al. |
| 6,052,191 | A | 4/2000 | Brayden et al. |
| 6,330,387 | B1 | 12/2001 | Salamon et al. |
| 6,441,375 | B1 | 8/2002 | Joseph et al. |
| 6,784,431 | B2 | 8/2004 | Shelley et al. |
| 2003/0001119 | A1 | 1/2003 | Takezawa et al. |
| 2003/0230720 | A1 | 12/2003 | Shelley et al. |
| 2003/0232448 | A1 | 12/2003 | Shelley et al. |
| 2004/0099807 | A1 | 5/2004 | Shelley et al. |

FOREIGN PATENT DOCUMENTS

WO  WO 01/92820 A1  12/2001

OTHER PUBLICATIONS

Carmer, et al., "Low-Cost Quality Control and Nondestructive Evaluation Technologies for General Aviation Structures", NASA/TM—1998-208456, Jul. 1998.

(Continued)

*Primary Examiner*—Constantine Hannaher
(74) *Attorney, Agent, or Firm*—Lee & Hayes, PLLC

(57) ABSTRACT

The the thickness of an opaque coating may be measured using near-infrared absorbance. One measurement method includes transmitting the near-infrared radiation towards the opaque material and determining relative absorbance levels over a range of near-infrared wavelengths. Absorbance wavelengths having relatively high absorbance and relatively low absorbance are then identified and selected. The selected wavelength values are then correlated with known material thicknesses.

21 Claims, 6 Drawing Sheets

OTHER PUBLICATIONS

Kumar et al, "Studies on Anodic Oxide Coating with Low Absorptance and High Emittance on Aluminum Alloy 2024", Solar Energy Material & Solar Cells 60 (2000) p. 51-57, Received Feb. 22, 1999, received in revised form Apr. 12, 1999, accepted Jun. 1, 1999, www.elsevier.com.

Kumar et al., "Studies on White Anodizing on Aluminum Alloy for Space Applications", Applied Surface Science 151 (1999) p. 280-286, Received Mar. 20, 1999, accepted May 31, 1999, www.elsevier.nl/locate/apsusc.

Lee et al., "Thickness Measurement of Titanium and Titanium Silicide films by Infrared Transmission", J. Vac. Sci. Technol., 6:5 (Sep./Oct. 1988) pp. 1533-1536.

Ramis et al., "Polyurethane-Unsaturated Polyester Interpenetrating Polymer Networks: Thermal and Dynamic Mechanical Thermal Behaviour", Polymer 42 (2001), 9469-9479.

Schram et al., "Nondestructive Optical Characterization of Conversion Coatings on Aluminum", J. Electrochem. Soc., 145:8 (Aug. 1998) pp. 2733-2739.

* cited by examiner

METHOD OF MEASURING THICKNESS OF AN OPAQUE COATING USING NEAR-INFRARED ABSORBANCE

RELATED APPLICATIONS

This patent application is a continuation in part of U.S. patent application Ser. No. 10/304,640 entitled "Method of Measuring Thickness of an Opaque Coating Using Infrared Absorbance" filed on Nov. 26, 2002 now U.S. Pat. No. 6,903,339, and is also related to a U.S. patent application Ser. No. 10/304,627 entitled "Method of Measuring Amount of Chemical Cure and Amount of Surface Contamination Using Infrared Absorbance" filed on Nov. 26, 2002, which applications are hereby incorporated by reference.

FIELD OF THE INVENTION

This invention relates generally to measuring a coating thickness and, more specifically, to measuring a thickness of an opaque coating.

BACKGROUND OF THE INVENTION

Surfaces of many different materials are coated in a variety of applications for aesthetic reasons and also for protecting a surface of an underlying substrate. For a number of reasons, it is desirable to determine a thickness of the coating applied to the surface.

For example, it may be desired to apply at least a minimum, predetermined thickness of a coating, such as a paint or a primer material on the surface, since optimal adhesion of the paint coating is generally a function of the paint thickness. In addition, applying at least a minimum thickness of paint or primer to a surface ensures that any underlying visual features on the surface do not "bleed through" the coating. This may be important in instances where projecting a professional image to customers is important, and to instill a feeling of customer confidence, such as through company signage or commercial airline tail art. This is also important for ensuring that a product, such as a motor vehicle or an airplane, displays a finish quality that is favored by the customer.

Further, applying at least a minimum thickness of the paint or primer may also provide a desired amount of protection from corrosion, or other deterioration of the underlying surface and substrate. For example, many surfaces that are painted are subject to environments that are conducive to corrosion, such as marine vessels that operate in water, which may include salt water. Further, motor vehicles and airplanes often operate in rainy or humid environments. Therefore, it is desirable to provide at least a minimum amount of protection against the corrosive effects of these environments.

In some applications, weight is an important consideration. For example, it is desirable to minimize weight of an airplane to reduce fuel consumption. Since the exterior surface area ("wetted area") of the airplane may be significantly large, a paint and primer applied to the exterior surface can be a significant factor in the total weight of the airplane.

Therefore, it may also be desired in some applications to limit thickness of paint or primer coating on a surface to a predetermined maximum thickness.

In order to ensure that a minimum, predetermined thickness of paint or primer coating is applied and that a maximum, predetermined thickness of paint or primer coating is not exceeded, it would be desirable to nondestructively determine thickness of a paint or primer coating on a surface. Currently known nondestructive measurement techniques are limited in their applicability.

In one known method, eddy current testing is used to determine paint thickness on metal substrates. As is known, eddy current testing detects electrical currents, known as eddy currents that propagate within the metal substrate. As a result, eddy current testing can only be used to determine thickness of paint or primer that is coated onto a surface of a metal substrate.

In another known method, ultrasound testing is used to determine thickness of a paint or primer coating on a surface of a composite or plastic substrate. However, ultrasound testing is not as reliable as eddy current testing, and also exhibits reduced accuracy for coating thicknesses below approximately 0.002 inches ("2 mils").

Therefore, there is an unmet need in the art for a simple, reliable, nondestructive method for determining a paint thickness regardless of the substrate on which the paint is coated.

SUMMARY

The present invention comprises methods for measuring the thickness of an opaque coating using near-infrared infrared absorbance. In one aspect, a method includes transmitting the near-infrared radiation towards the opaque material and determining relative absorbance levels over a range of near-infrared wavelengths. Absorbance wavelengths having relatively high absorbance and relatively low absorbance are then identified and selected. The selected wavelength values are then correlated with known material thicknesses.

BRIEF DESCRIPTION OF THE DRAWINGS

Embodiments of the present invention are described in detail below with reference to the following drawings.

DETAILED DESCRIPTION

The present invention relates to methods for measuring a thickness of an opaque coating using near-infrared wavelengths. Many specific details of certain embodiments of the invention are set forth in the following description and in FIGS. 1 through 8 to provide a thorough understanding of such embodiments. One skilled in the art, however, will understand that the present invention may have additional embodiments, or that the present invention may be practiced without several of the details described in the following description.

Figure 1:
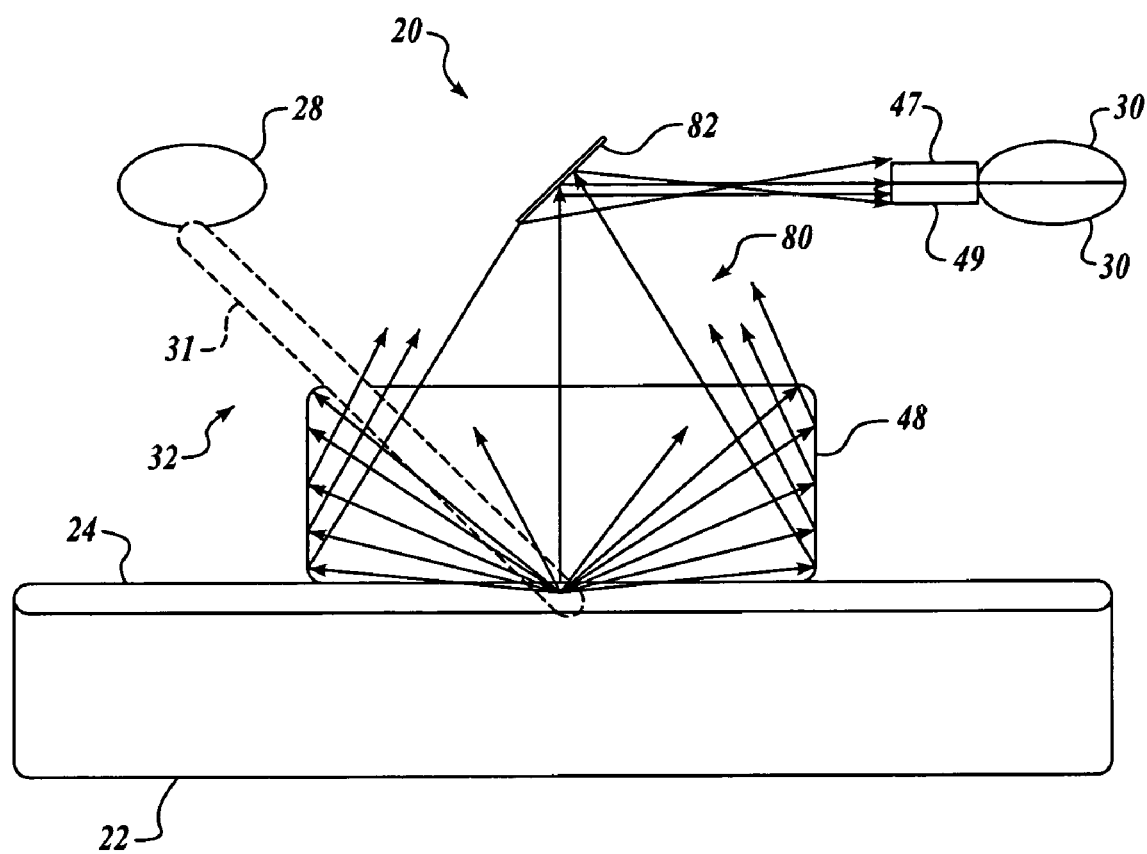
FIG. 1 is a side view of a testing setup for determining the thickness of an opaque coating in accordance with an embodiment of the present invention.

The various embodiments of the present invention provide methods for nondestructively determining a thickness of an opaque coating, such as a paint or a primer coating applied to a surface. In general, embodiments of the present invention may determine the thickness of the opaque coating by correlating a difference between an infrared absorbance of the opaque coating at various predetermined wavelengths to the thickness of the opaque coating regardless of the substrate. With reference now to FIG. 1, a particular embodiment of the present invention determines a thickness of an opaque coating using a testing setup 20. Initially, a base reference value of infrared energy reflected by a scattering reference substrate is obtained. The reference substrate does not include a surface coating. Accordingly, an infrared transmission beam 31 is transmitted from an infrared source 28 along a predetermined incident beam path 32 and into a diffuse reflectance collector 48 that is placed in contact with the scattering reference substrate. Alternately, an integrating sphere may also be used instead of the diffuse reflectance collector 48. In either case, the infrared beam 31 is scattered by the scattering reference substrate and is collected by the collector 48. Collected infrared beams 80 exit the collector 48, are reflected by a reflector 82, and are filtered at different wavelength ranges by a plurality of optical bandpass filters 47. At least one infrared detector 30 then detects the filtered infrared beams. The scattering reference substrate is suitably a rough surface, such as without limitation a zero-sintered gold-coated surface having particles that are approximately the same size as particles of the opaque coating to be measured.

A substrate 22 with a sample of an opaque coating 24, such as paint or primer, is put into contact with the collector 48 and the infrared beam 31 is transmitted into the collector 48 as described above. The infrared beam 31 is scattered by the opaque coating 24 and is collected by the collector 48. Collected infrared beams 37 exit the collector 48, are reflected by the reflector 82, and are filtered at the different wavelength ranges by the plurality of filters 47. The filtered infrared beams are then detected by the at least one infrared detector 30. A comparison is made of the infrared energy of the collected infrared beams 80 scattered by the coating 24 and the infrared energy of the base reference value to determine two different absorbance values. A difference between these absorbance values is correlated to absorbance values of known thicknesses of opaque coatings and the thickness of the opaque coating is determined. Specific details of the testing setup 20 will be described in further detail below.

In one particular embodiment, the measurement of the coating thickness is conducted for a coating 24 that includes a polyurethane-based paint on a composite substrate 22. It is understood, however, that measurements for other opaque coatings 24, such as other paint materials and primers, including epoxy primers, latex paint, enamel paint, filled stains and varnishes, and other like coatings, may also be made. Additionally, other substrates 22 may include various composite resins, thermoforming and thermosetting plastics, wood, fiberglass, and other similar materials, and are considered within the scope of the present invention. In order to measure the thickness of other opaque coatings 24 that are not illustrated herein, one simply selects suitable wavelength infrared absorbance bands that change with each different material used for the opaque coating 24.

In one particular embodiment, the testing setup 20 is suitably a simple infrared filter spectrometer system, including the infrared source 28, infrared beam optics, the collector 48 that contacts the sample or coating 24, the reflector 82, the filters 47, the detector 30, and a data system (not shown). One example of a simple infrared filter spectrometer system is a Coating Weight Reader produced by Personal Instruments, although it is understood that other infrared systems are employable with the testing setup 20, such as, without limitation, standard Fourier transform infrared spectrometers and infrared imaging systems. An example of a suitable standard Fourier transform infrared spectrometer is the Thermo Nicolet Model 760 FT-IR spectrometer system fitted with a diffuse reflectance collector accessory and a Surface Optics Corporation SOC400 portable FT-IR spectrometer with a diffuse reflectance collector attachment. Non-limiting examples of infrared imaging systems employable with the present invention include IMAGEMAX produced by the Thermo Electron Corporation of Waltham Mass. It will be appreciated that the various infrared systems may be as used in-line production elements or may be a portable, hand-held arrangement.

In one particular embodiment, the infrared beam 31 is suitably transmitted as a broadband near-infrared light beam having wavelengths in a range between approximately about 0.7 and approximately about 2.4 microns ($\mu$m). The collected beams 80 are suitably filtered by the plurality of filters 47 that admit selected wavelength bands. Accordingly, the wavelength bands may have center wavelengths that range between approximately about 1400 nanometers (nm) and approximately about 2500 nm. More specifically, the center wavelengths may range between approximately about 1000 nm and approximately about 2000 nm. In another particular embodiment, the plurality of filters 47 includes at least six optical filters. In still another embodiment, a first filter is centered at a wavelength of about 1600 nm, a second filter is centered at a wavelength of about 1700 nm, a third filter is centered at a wavelength of about 1900 nm, a fourth filter is centered at a wavelength of about 1970 nm, a fifth filter is centered at a wavelength of about 2020 nm, and a sixth filter is centered at a wavelength of about 2225 nm. It will be appreciated that the filters 47 may act on either the transmitted beam 31 or the collected beams 80. It will be further appreciated that an optimal wavelength for a desired application may deviate from the wavelengths described above depending on the material to be measured. Further, it will be appreciated that when using either standard infrared spectrometer or infrared imaging systems, the filters 47 may suitably be implemented by hardware or software performing the same filtering function.

Figure 2:
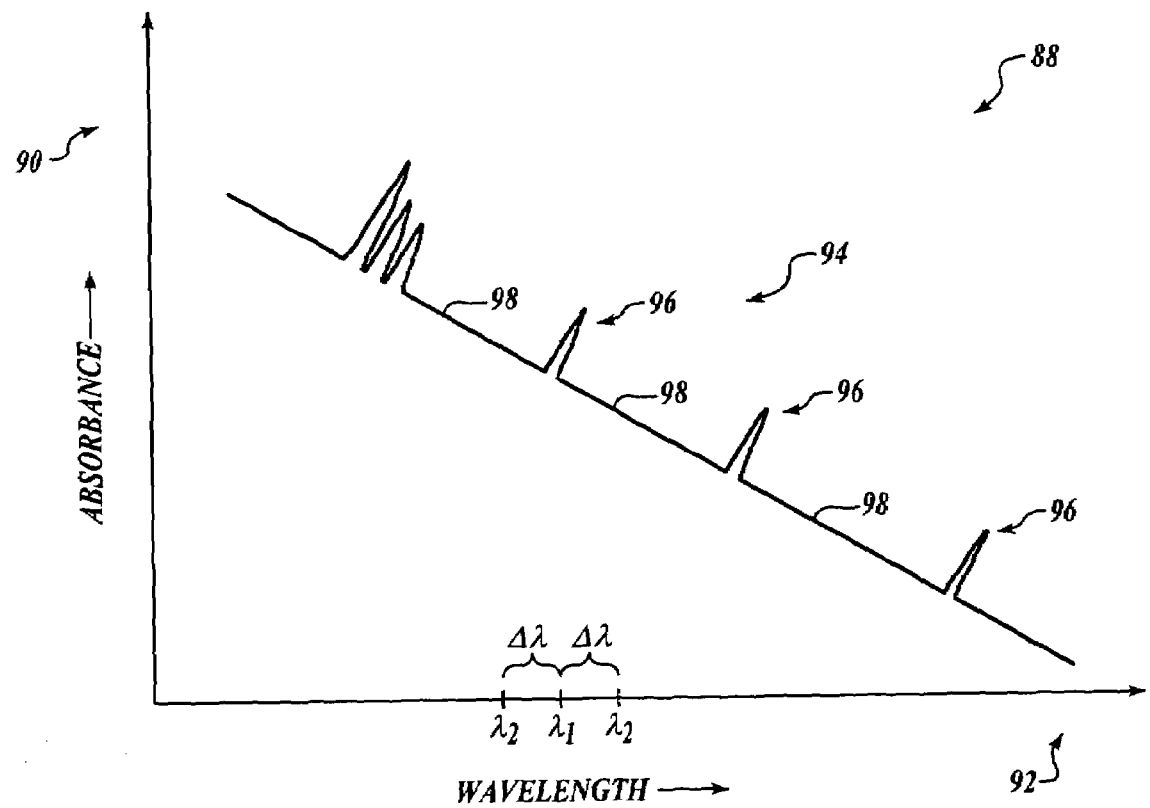
FIG. 2 is a graph of absorbance versus frequency.

According to the various embodiments of the present invention, measurement of the thickness of the opaque coating takes advantage of changes in scattering as the wavelength of the infrared radiation varies. Referring now to FIG. 2, a graph 88 shows a curve 94 of absorbance of infrared energy in an opaque coating 24 along a Y-axis 90 versus the infrared wavelength along an X-axis 92. As wavelength decreases, wavelength of the infrared energy becomes comparable to size of particles within the opaque coating 24. As a result, scattering of the infrared energy increases. Because the total reflectance remains relatively constant, increased scattering results in decreased specular reflectance, so that the absorbance values increase. Conversely, as the wavelength increases, the wavelength of the infrared energy becomes less comparable to the size of particles within the opaque coating 24. As a result, scattering decreases. Because the total reflectance remains constant, a decrease in scattering results in an increase in specular reflectance. Accordingly, detection of infrared energy of the specular component of reflected infrared energy increases and absorbance values decrease. Therefore, the curve 94 has a negative slope as wavelength increases.

Advantageously, the present invention measures the specular component of reflected infrared energy at a plurality of selected near infrared wavelengths to compensate for changes in specular reflection due to changes in scattering. Absorbance peaks 96 are detected at a first wavelength $\lambda_1$ for the sample being measured. The first wavelength $\lambda_1$ occurs where absorbance is expected for the sample being measured. As discussed above, magnitude of the absorbance of the specular component generally decreases as wavelength increases. However, the magnitude of the absorbance peaks 96 relative to a baseline 98 (where no absorbance in the sample being measured is expected) remains unaffected by scattering. Therefore, according to the invention, energy of the specular component is additionally detected at a second wavelength $\lambda_2$ where absorbance is not expected for the sample being measured. The second wavelength $\lambda_2$ is offset from the first wavelength $\lambda_1$ by a wavelength difference $\Delta\lambda$. It will be appreciated that the second wavelength $\lambda_2$ is suitably greater than the first wavelength $\lambda_1$ or is suitably less than the first wavelength $\lambda_1$, as desired for a particular application. Advantageously, comparing magnitude of the absorbance peak 96 at the first wavelength $\lambda_1$ to magnitude of absorbance at the second wavelength $\lambda_2$ compensates for the negative slope of the curve 94 due to scattering. It is understood that the foregoing procedure may be repeated at other selected wavelengths in order to identify a selected opaque coating. For example, a plurality of selected wavelengths may be employed so that more than one wavelength difference a may be calculated. The calculated wavelength differences $\Delta\lambda$ may be then be cooperatively employed to determine the thickness of the opaque coating. Alternately, the first wavelength $\lambda_1$ may be combined with the second wavelength $\lambda_2$ to form a ratio of the first wavelength $\lambda_1$ and the second wavelength $\lambda_2$ that may be correlated with the thickness of the opaque layer.

Referring again to FIG. 1, the broadband infrared beam 31 is generated by the infrared source 28. The infrared source 28 is any acceptable source of infrared energy known in the art that can produce the infrared beam 31 having a desired wavelength. One suitable example of a preferred embodiment of the infrared source is the ReflectIR-PIN source made by Ion Optics, Incorporated of Waltham, Mass., although other suitable alternatives exist. The infrared detectors 30 in the filtered systems described here are suitably arranged to detect the collected beams 80. One suitable example of the infrared detectors 30 is an Eltec Corp 406MAY-XXX where XXX indicates the filters that are used with the detectors 30.

The diffuse reflectance collector 48 is suitably any acceptable reflectance collector known in the art. For example, the diffuse reflectance collector is suitably a barrel ellipse diffuse reflectance collector, such as a diffuse reflection head available from Surface Optics Corp. The particles within the opaque coating 24 scatter infrared beams 80 at a variety of random angles. Advantageously, the diffuse reflectance collector 48 detects the scattered infrared beams 80 from the variety of random angles, collects the scattered infrared beams 80, and sends the scattered infrared beams 80 to a focal point.

Advantageously, the reflector 82 may be placed at approximately the focal point of the diffuse reflectance collector 48. The reflector 82 is placed at a suitable angle to reflect the collected scattered infrared beams 80 toward the plurality of filters 47. The reflector 82 is suitably any reflector surface having acceptable reflective properties, such as a mirror, any highly polished surface, or the like. In another embodiment of the invention, an integrating sphere may replace the diffuse reflectance collector 48 so that beams 80 having a relatively low intensity may be measured. In either case, it will be appreciated that the setup 20 is not depicted to scale in FIG. 1. Instead, the diffuse reflectance collector 48 and the reflector 82 are shown greatly enlarged to clearly depict ray paths of the infrared beams 31 and 80.

Figure 3:
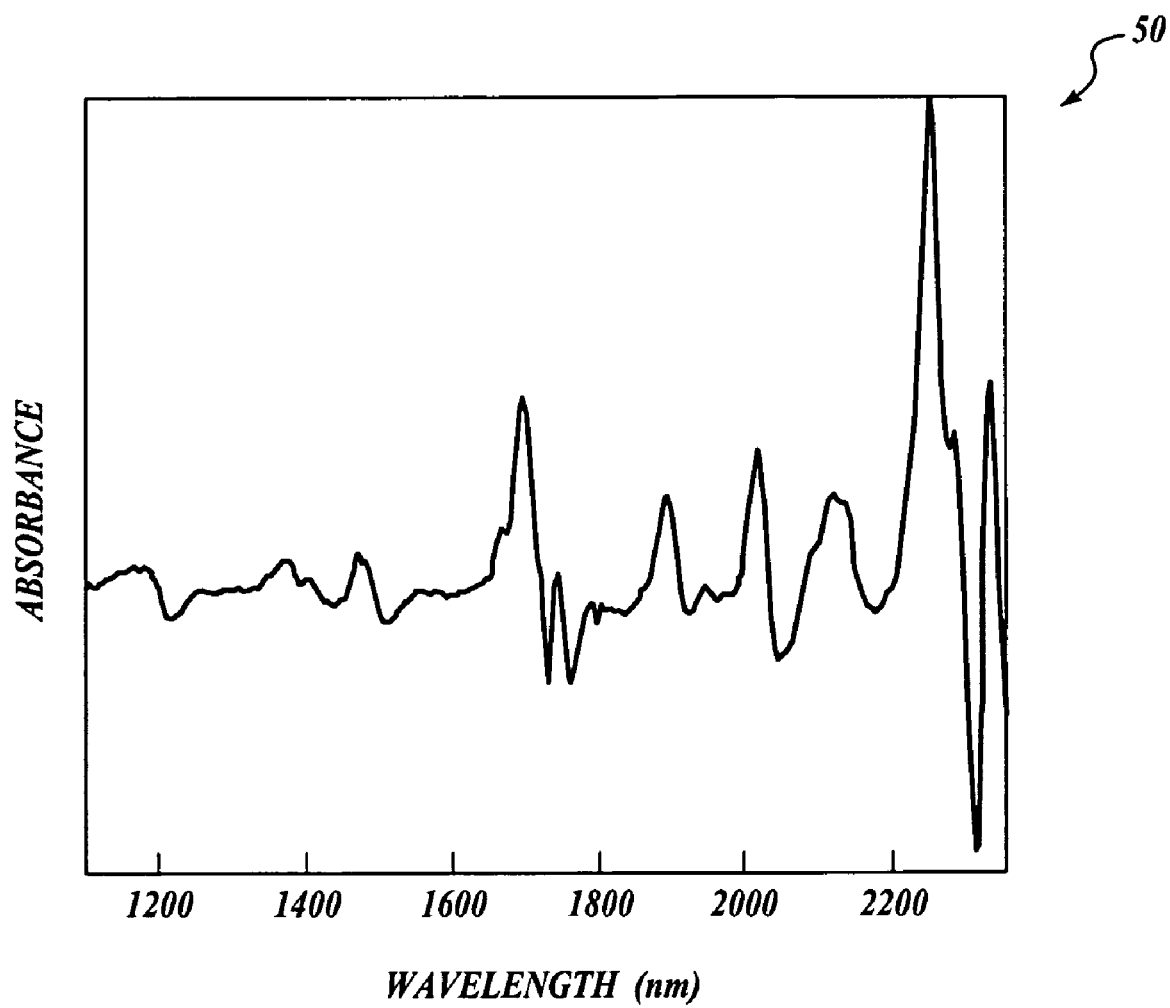
FIG. 3 is an exemplary absorbance spectrograph for an opaque coating applied to a composite substrate.

FIG. 3 is an exemplary absorbance spectrograph 50 for an opaque coating applied to a composite substrate. The spectrograph 50 includes a plurality of absorbance peaks that appear at different near-infrared wavelengths. Accordingly, relative absorbance peaks are observed at approximately about 1700 nm, 1900 nm, 2020 nm and 2225 nm, while at other wavelengths, such as approximately about 1600 nm and 1970 nm, relatively little infrared energy is absorbed.

Figure 4:
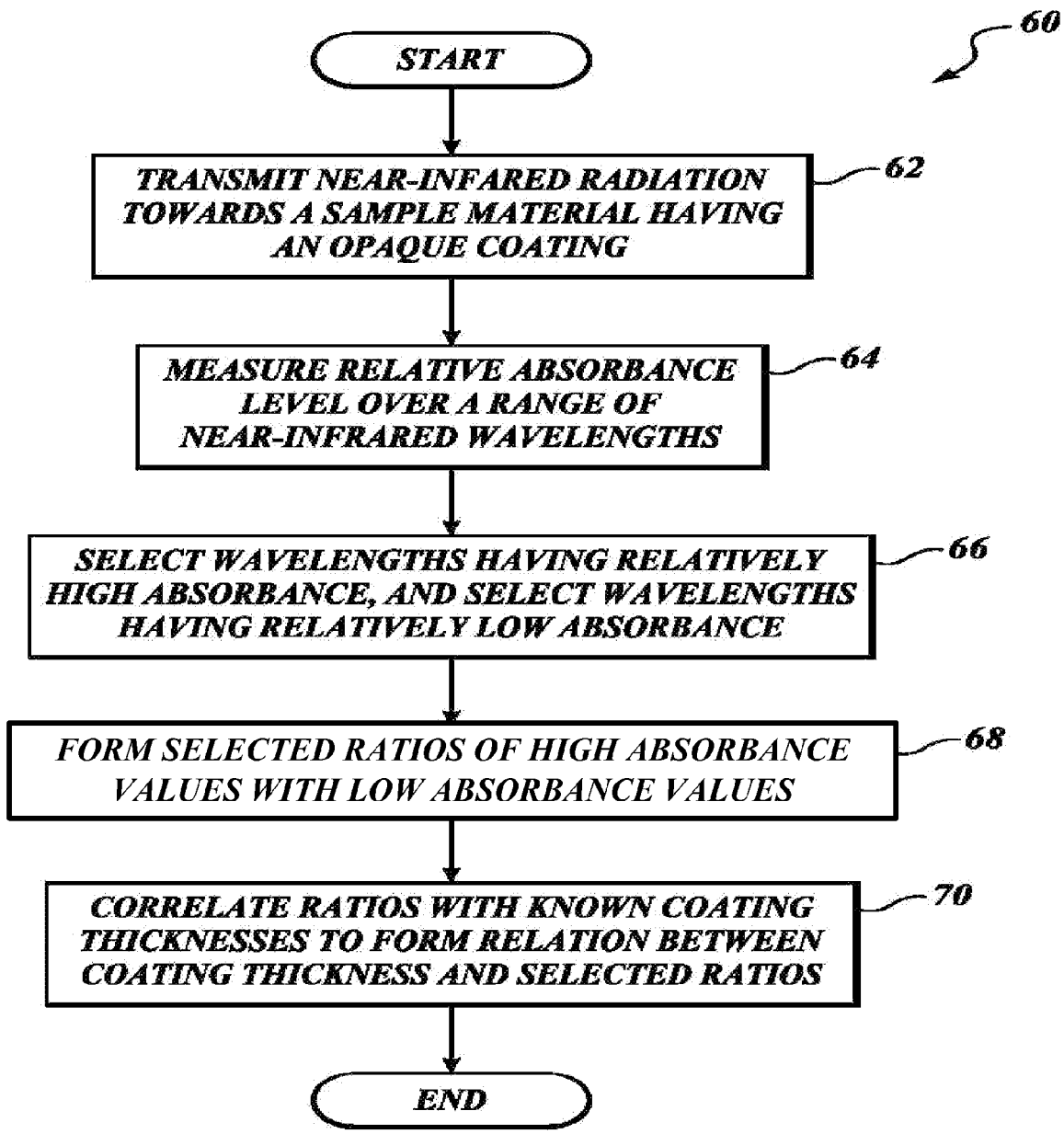
FIG. 4 is a flowchart of a method for determining the thickness of a coating according to an embodiment of the invention.

With continuing reference to FIG. 1 through FIG. 3, and turning now to FIG. 4, a method 60 for determining the thickness of a coating is shown, according to an embodiment of the invention. At block 62, near-infrared radiation is directed towards a sample material having an opaque coating, which may include one or more discrete layers. The near-infrared radiation may be directed towards the sample material by the apparatus shown in FIG. 1, or by other similar devices. At block 64, the relative absorbance levels over a range of near-infrared wavelengths are measured. Accordingly, an absorbance spectrograph similar to the spectrograph 50 shown in FIG. 3 is generated. At block 66, wavelengths having relatively high absorbance and relatively low absorbance are identified. For example, in the particular embodiment described above and shown in FIG. 3, relatively high absorbance values are present at wavelengths of approximately about 1700 nm, 1900 nm, 2020 nm and 2225 nm. In contrast, relatively low absorbance values are present at wavelengths of approximately about 1600 nm and 1970 nm. At block 68, selected peak absorbance values are combined with selected absorbances of relatively low value to form absorbance ratios. In one particular embodiment, peak absorbance values are combined with adjacent low absorbance values to form the desired ratios. For example, and with reference again to FIG. 3, the absorbance at about 1700 nm may be combined with the absorbance value at about 1600 nm to form a first ratio, the absorbance values at about 1900 nm, 2020 nm and 2225 nm may be combined with the absorbance value at about 1970 nm to yield second, third and fourth ratios, respectively. At block 70, the ratios formed at block 68 are correlated with known coating thicknesses on the sample. The reference material thicknesses may be determined by any of a variety of known thickness determination methods. For example, a reference material thickness of an opaque layer may be determined using the destructive or non-destructive methods previously described in the background section above, or by using an ultrasound method. One suitable ultrasound device to determine a reference material thickness is the Panametrics NDT Model 25 ultrasound thickness detector, available from Panametrics NDT, Incorporated, of Waltham, Mass., although other suitable methods and devices exist.

Figure 5:
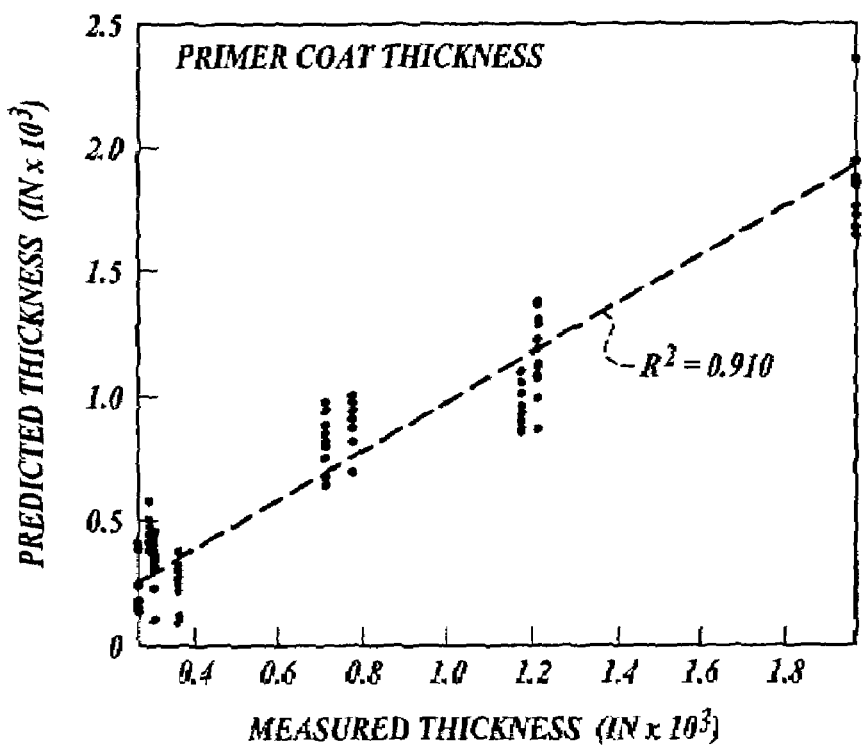
FIG. 5 is an exemplary and graphical view of a scatter plot that compares a measured primer coat thickness and a predicted primer coat thickness.

FIG. 5 is an exemplary and graphical view of a scatter plot that compares a measured primer coat thickness and a predicted primer coat thickness based upon the correlation discussed above. In the present example, the primer coat is applied to a polymer-based and fiber reinforced composite material. The various data points shown in FIG. 5 represent absorbance values obtained at selected wavelengths, as described above. In the present example, a linear regression method was employed to correlate the data, although other known correlation methods may also be used. The linear regression method yields a correlation coefficient ($R^2$) of 0.91, indicating that favorable correlation between measured primer thickness and the predicted thickness.

Figure 6:
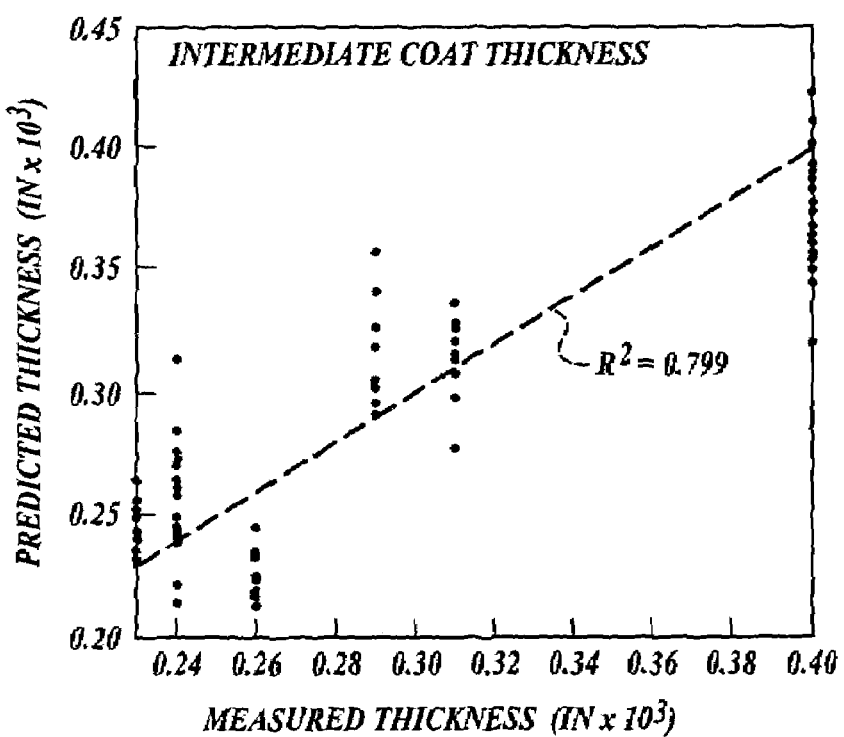
FIG. 6 is an exemplary and graphical view of a scatter plot that compares a measured intermediate coat thickness and a predicted intermediate coat thickness.

FIG. 6 is an exemplary and graphical view of a scatter plot that compares a measured intermediate coat thickness and a predicted intermediate coat thickness. In the present example, the intermediate coat is applied to the foregoing polymer-based and fiber reinforced composite material. A generally acceptable material thickness correlation is achieved using a linear regression method, as evidenced by the correlation coefficient ($R^2$) of 0.799.

Figure 7:
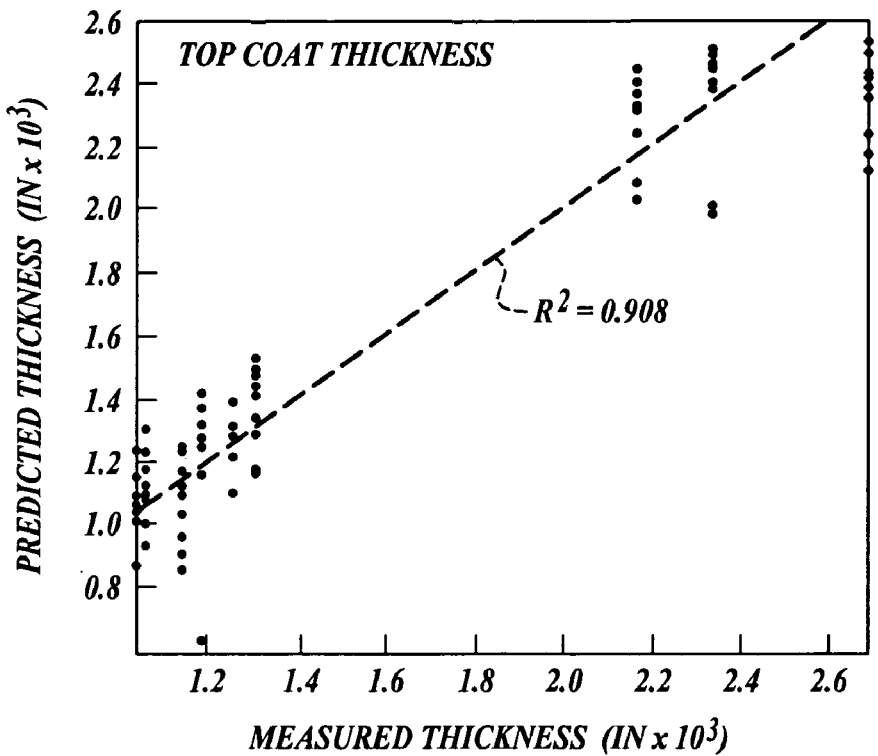
FIG. 7 is an exemplary and graphical view of a scatter plot that compares a measured finish coat thickness and a predicted finish coat thickness.

FIG. 7 is an exemplary and graphical view of a scatter plot that compares a measured finish coat thickness and a predicted finish coat thickness. The data shown in FIG. 7 represent absorbance values obtained when the finish coat is applied to the foregoing polymer-based and fiber reinforced composite material. Again, a favorable material thickness correlation is achieved using linear regression, as evidenced by the correlation coefficient ($R^2$) of 0.908.

Figure 8:
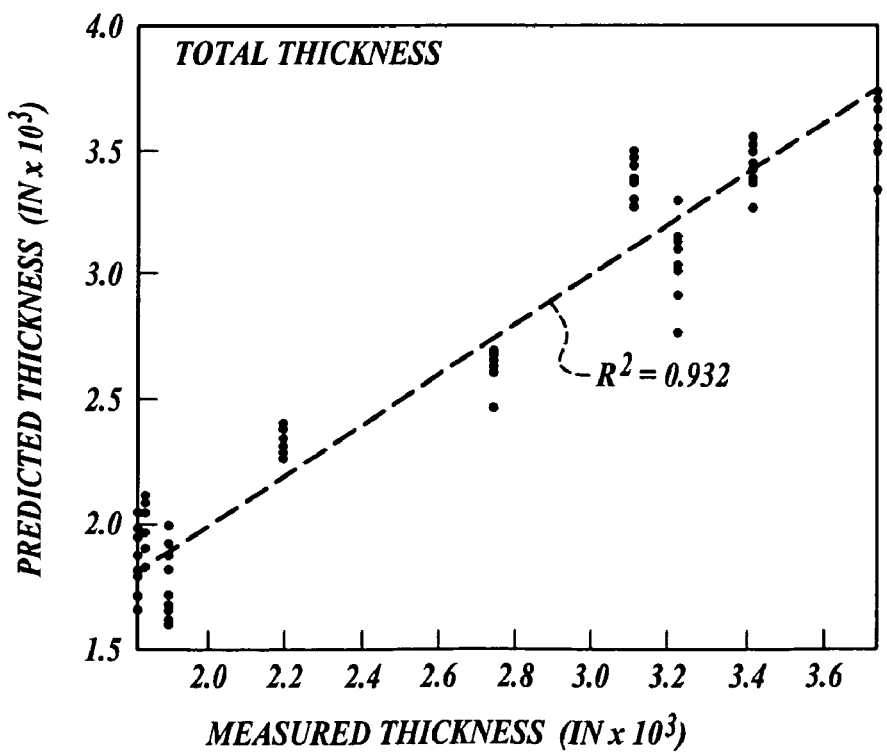
FIG. 8 is an exemplary and graphical view of a scatter plot that compares a measured multiple coat thickness and a predicted multiple coat thickness.

FIG. 8 is an exemplary and graphical view of a scatter plot that compares a measured total coat thickness and a predicted total coat thickness. The data shown in FIG. 7 represent absorbance values obtained when all of the foregoing material layers (i.e. the primer coat, the intermediate coat and the finish coat) are applied to the polymer-based and fiber reinforced composite material. Again, a favorable material thickness correlation is achieved using linear regression, as evidenced by the correlation coefficient ($R^2$) of 0.908.

The foregoing compilation and linear regression calculation may be performed in a number of suitable ways. For example, and in one particular embodiment, the compilation and calculation may be performed by a processor, such as a microprocessor (not shown) that is operable to perform pre-programmed mathematical operations. Any processor known in the art is acceptable such as, without limitation, a PENTIUM-series processor available from Intel Corporation of Santa Clara, Calif., although other suitable alternatives exist. The processor is suitably included within the infrared spectrometer and is also suitably provided as a stand-alone unit that is electrically coupled to receive data from the infrared detectors 30 (FIG. 1). Alternately, the calculation is performed by an electronic computer chip or is performed manually. The results of the calculation yield the desired absorbance ratios and also calculate the correlation for the thickness of the opaque coating.

While preferred and alternate embodiments of the invention have been illustrated and described, as noted above, many changes can be made without departing from the spirit and scope of the invention. Accordingly, the scope of the invention is not limited by the disclosure of these preferred and alternate embodiments. Instead, the invention should be determined entirely by reference to the claims that follow.

What is claimed is:

1. A method of measuring a thickness of an opaque material applied to a substrate, comprising:
    transmitting radiation at a near-infrared wavelength towards the opaque material;
    determining relative absorbance levels over a range of the near-infrared wavelengths;
    identifying absorbance wavelengths having at least one of relatively high absorbance and relatively low absorbance;
    selecting absorbance values corresponding to the identified wavelengths; and
    correlating the selected wavelength values with known material thicknesses,
    wherein correlating the selected wavelength values further comprises forming selected ratios of the absorbance values.

2. The method of claim 1, wherein forming selected ratios of the absorbance values further comprises selecting at least one value having a relatively high absorbance and forming a ratio with a value having a relatively low absorbance.

3. The method of claim 1, wherein transmitting radiation at a near-infrared wavelength further comprises emitting the radiation at a wavelength in the range of between approximately about 0.7 and approximately about 2.4 microns.

4. The method of claim 1, wherein determining relative absorbance levels over a range of the near-infrared wavelengths further comprises detecting absorbance values at a wavelength in the range of between approximately about 1700 nanometers and approximately about 2000 nanometers.

5. The method of claim 4, wherein detecting absorbance values at a wavelength in the range of between approximately about 1000 nanometers and approximately about 2000 nanometers further comprises detecting the absorbance values using a plurality of optical filters having selected center wavelength values operable to transmit radiation at about the selected center wavelength values.

6. The method of claim 5, wherein detecting the absorbance values using a plurality of optical filters having selected center wavelength values further includes selecting at least six optical filters.

7. The method of claim 6, wherein selecting at least six optical filters further comprises selecting a first filter having a center wavelength of approximately about 1600 nanometers, a second filter having a center wavelength of approximately about 1700 nanometers, a third filter having a center wavelength of approximately about 1900 nanometers, a fourth filter having a center wavelength of approximately about 1970 nanometers, a fifth filter having a center wavelength of approximately about 2020 nanometers, and a sixth filter having a center wavelength of approximately about 2225 nanometers.

8. The method of claim 1, wherein determining relative absorbance levels over a range of the near-infrared wavelengths further comprises collecting reflected near-infrared radiation in a reflectance collector.

9. The method of claim 8, wherein collecting reflected near-infrared radiation in a reflectance collector further comprises collecting the reflected radiation in a barrel ellipse diffuse reflectance collector.

10. The method of claim 8, wherein collecting reflected near-infrared radiation in a reflectance collector further comprises collecting the reflected radiation in an integrating sphere.

11. A method of measuring a thickness of one or more opaque coating materials applied to a supporting composite material, comprising:
    projecting near-infrared radiation towards the one or more opaque coating materials;
    collecting near-infrared radiation reflected from a surface of the one or more opaque coating materials;

filtering the collected near-infrared radiation at selected wavelengths to obtain absorbance values having at least one of relatively high absorbance and relatively low absorbance; and correlating the absorbance values with corresponding reference values of known material thicknesses of the opaque coating material, wherein correlating the relatively high absorbance values and the relatively low absorbance values further comprises forming ratios of the high absorbance values with the low absorbance values.

12. The method of claim 11, wherein projecting near-infrared radiation towards the one or more opaque coating materials further comprises emitting broadband near-infrared radiation having a wavelength in a range between approximately about 0.7 microns and approximately about 2.4 microns.

13. The method of claim 11, wherein collecting near-infrared radiation reflected from a surface of the one or more opaque coating materials further comprises collecting the reflected near-infrared radiation in a reflectance collector.

14. The method of claim 13, wherein collecting the reflected near-infrared radiation in a reflectance collector further comprises collecting the radiation in a barrel ellipse diffuse reflectance collector.

15. The method of claim 13, wherein collecting the reflected near-infrared radiation in a reflectance collector further comprises collecting the radiation in an integrating sphere.

16. The method of claim 11, wherein filtering the collected near-infrared radiation at selected wavelengths further comprises selecting at least six filters having center wavelengths that range between approximately about 1600 nanometers to approximately about 2225 nanometers.

17. The method of claim 11, wherein the one or more opaque materials further comprises one of a primer coating, an intermediate coating and a finish coating.

18. The method of claim 11, wherein forming ratios of the high absorbance values with the low absorbance values further comprises performing a linear regression on the formed ratios.

19. A method of measuring a thickness of an opaque material applied to a substrate, comprising:

transmitting near-infrared radiation towards the opaque material;

identifying absorbance wavelengths having at least one of relatively high absorbance and relatively low absorbance;

selecting absorbance values corresponding to the identified absorbance wavelengths;

forming ratios of the selected absorbance values; and correlating the ratios with known material thicknesses.

20. The method of claim 19, wherein forming ratios of the high absorbance values with the low absorbance values further comprises performing a linear regression on the formed ratios.

21. The method of claim 19, further comprising determining relative absorbance levels over a range of the near-infrared wavelengths.

* * * * *